US005534551A

United States Patent [19]

Page et al.

[11] Patent Number: 5,534,551
[45] Date of Patent: Jul. 9, 1996

[54] AMINOGUANIDINE SPRAY DRYING PROCESS

[75] Inventors: Phillip E. Page, Lee's Summit, Mo.; Jonathan Berman, Lenexa, Kans.; Janet M. Pence, Raymore; Sharon K. Minish, Independence, both of Mo.

[73] Assignee: Hoechst Marion Roussel, Inc., Cincinnati, Ohio

[21] Appl. No.: 318,754

[22] PCT Filed: Mar. 24, 1993

[86] PCT No.: PCT/US93/02714

§ 371 Date: Dec. 22, 1994

§ 102(e) Date: Dec. 22, 1994

[87] PCT Pub. No.: WO93/20808

PCT Pub. Date: Oct. 28, 1993

Related U.S. Application Data

[63] Continuation-in-part of Ser. No. 869,558, Apr. 15, 1992, abandoned.

[51] Int. Cl.$^6$ .................................................. A61K 31/155
[52] U.S. Cl. ........................................... 514/634; 424/465
[58] Field of Search ............................... 514/634; 424/465

[56] References Cited

U.S. PATENT DOCUMENTS

| | | |
|---|---|---|
| 3,621,056 | 11/1971 | Houlihan et al. . |
| 3,659,016 | 4/1972 | Manning . |
| 3,714,363 | 1/1973 | Manning . |
| 4,374,082 | 2/1983 | Hochschild et al. . |
| 4,519,961 | 5/1985 | Schumacher et al. . |
| 4,533,674 | 8/1985 | Schmidt et al. . |
| 4,605,666 | 8/1986 | Schmidt et al. . |
| 4,710,519 | 12/1987 | Finnan et al. . |
| 4,874,614 | 10/1989 | Becker et al. . |
| 4,892,889 | 1/1990 | Kirk et al. . |
| 4,916,163 | 4/1990 | Ni . |
| 5,002,774 | 3/1991 | Agrawala et al. . |
| 5,077,313 | 12/1991 | Lubec et al. . |

FOREIGN PATENT DOCUMENTS

| | | |
|---|---|---|
| 748407 | 2/1970 | Belgium . |
| 0222313 | 5/1987 | European Pat. Off. . |
| 0339496 | 11/1989 | European Pat. Off. . |
| 0436373 | 7/1991 | European Pat. Off. . |
| 2736064 | 2/1979 | Germany . |
| 64-56614 | 3/1989 | Japan . |
| 7317772 | 7/1974 | Netherlands . |

OTHER PUBLICATIONS

CA 114:10913 1990.
CA 112:42594 1989.
Ceramic Transactions, "In situ reaction via self–propagating chemical decomposition"—K. Kourtakis et al., AT&T Bell Labs—Ceram. Trans. (1990), 12 (Ceram. Powder Sci. 3), pp. 209–216.
Abstract—JP 3 206 034–A "Phenilamino: guanine derivatives compns. for e.g. ischaemic disease—comprises e.g. capsule contg. deriv. and mannitol"—Sep. 9, 1991—Assignee: Toyobo.
Abstract—1172–920–A "Mfr. of free–flowing choline–chloride powder—by spray–drying, with controlled dry additive contents, stage–wise cooling, and adding silicon–contg. cpd."—Aug. 15, 1985—Assignee: AS UKR Thermophys. Inst.
Abstract—50157–517–"Tablets contg. triglyceride cpds. which are really absorbed—made by spray–drying aq. suspension of triglyceride cpds. with e.g. casein, starch and dextrin"—Dec. 19, 1975—Assignee: Ono.
Abstract—71016–967–R "Aminoguanidine salts preparation"—May 11, 1971—Assignee: Shirai K, Oto K.
Abstract—01083–059 "Guanidine deriv. used as Maillard reaction inhibitor—obtd. by reacting a sulphonyl halide with a guanidine cpd."—Mar. 28, 1989—Assignee: Ono.
Abstract—01056–614–A "Maillard reaction inhibitors—contg. e.g. thiosemicarbazide or hydrazide der."—Mar. 3, 1989—Assignee: Ono.

*Primary Examiner*—Paul J. Killos
*Attorney, Agent, or Firm*—Carolyn D. Moon

[57] ABSTRACT

A compressed tablet comprising aminoguanidine or a pharmaceutically acceptable salt thereof and a suitably compatible binder prepared by spray drying techniques from an aminoguanidine solution, and methods of making same.

21 Claims, 1 Drawing Sheet

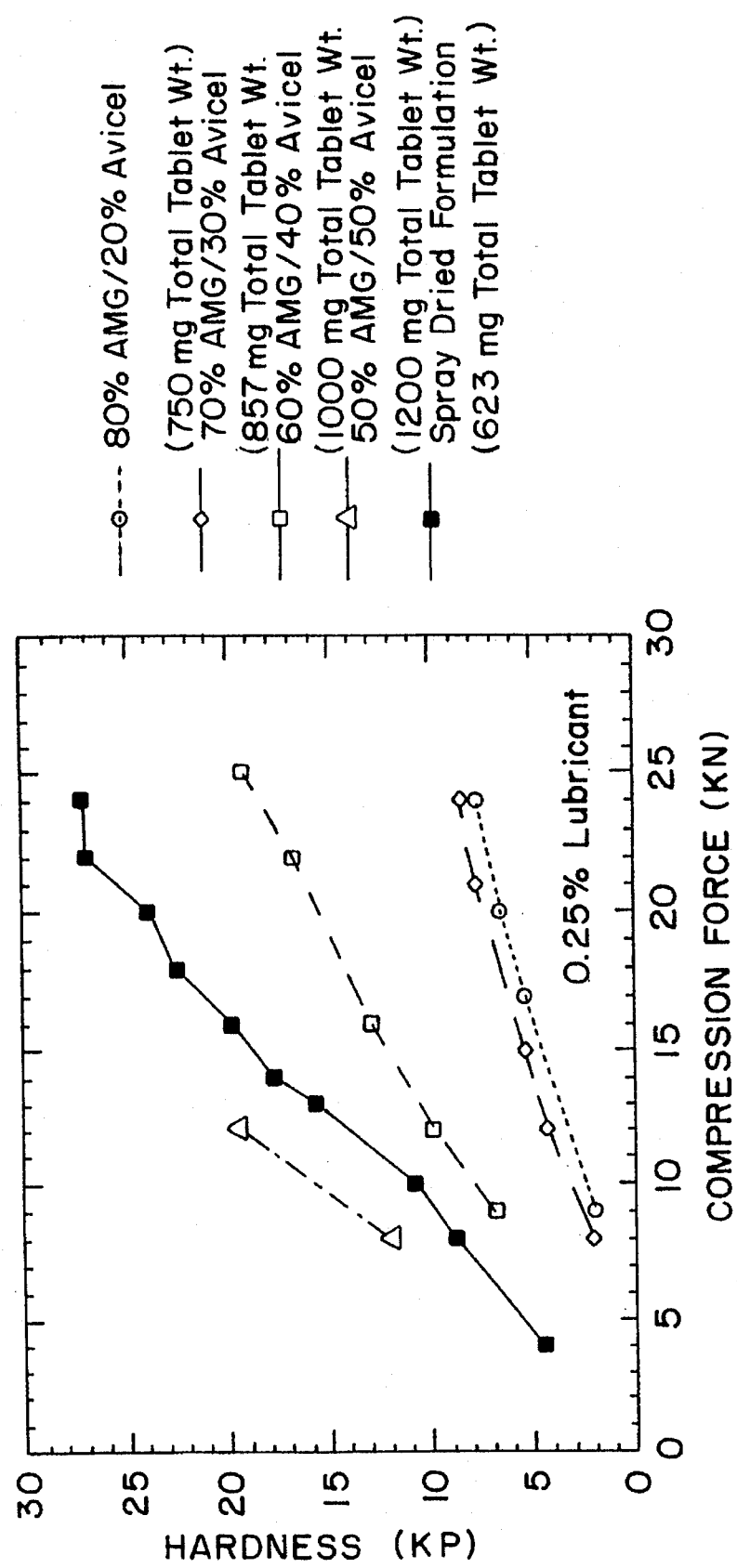

as# AMINOGUANIDINE SPRAY DRYING PROCESS

This is a continuation-in-part of U.S. Ser. No. 869,558, filed 15 April 1992 now abandoned and a (35 U.S.C.) 371 of application PCT/US93/02714, with an international filing date of 24 March 1993. This application is a 371 of PCT/US93/02714 Mar. 24, 1993.

FIELD OF THE INVENTION

The present invention is generally directed to pharmaceutical formulations comprising aminoguanidine for oral administration prepared with spray drying techniques to form direct compression tablets.

BACKGROUND OF THE INVENTION

Spray-drying techniques have been used in previous formulations, examples of which follow. However, spray-drying has not been reported in connection with aminoguanidine preparations.

U.S. Pat. No. 4,605,666 shows a preparation of vitamin powders by spray drying a slurry containing vitamin, binder, magnesium stearate and $SiO_2$.

U.S. Pat. No. 4,710,519 shows a preparation of acetaminophen powder by spray drying slurry of acetaminophena and binder and adding magnesium stearate and $SiO_2$.

U.S. Pat. No. 4,892,889 shows a preparation of vitamin powders by spray drying the mixture of vitamin, gelatin, carbohydrate, fatty acid monoglyceride, $SiO_2$ and water.

U.S. Pat. No. 4,519,961 shows a preparation of free-flowing powders of oxidation sensitive materials. Colloid suspension of a substance and one or more saccharides. The spray adjuvant is silicic acid and a metal salt of a higher fatty acid.

U.S. Pat. No. 4,916,163 shows an anti-diabetic compound containing glyburide, and spray dried lactose. Other excipients include $SiO_2$ and Magnesium Stearate.

JP Patent no. 03206034 shows a composition comprising aminoguanidine derivative and mannitol which can be in a tablet form.

SU Patent no. 1172920 shows the preparation of free-flowing cholin-chloride powder by spray drying.

U.S. Pat. No. 4,533,674 shows the preparation of vitamin C powder by spray drying a slurry of vitamin, binder and $SiO_2$.

JP 50157517 shows the preparation of triglyceride tablets by spray-drying a suspension of compounds with casein, starch and dextrin.

EP 436373 shows the preparation of naproxen tablets by spray drying slurry of compound or its salt and excipients.

Various patent applications and patents on aminoguanidine include JP 75001255, JP 71016967, EP 339496, JP 01083059, JP 01056614, DE 2736064, NL 7317772, U.S. Pat. No. 3,659,016, U.S. Pat. No. 3,714,363, BE 748407 and U.S. Pat. No. 3,621,056.

SUMMARY OF THE INVENTION

A method of making a direct compression tablet suitable for commercial pharmaceutical use comprising between about 50% to about 99% aminoguanidine or pharmaceutically acceptable salt thereof by weight of the tablet comprising:

combining a sufficient amount of aminoguanidine or a pharmaceutically acceptable salt thereof, a sufficient amount of an aqueous solution capable of substantially dissolving the aminoguanidine or pharmaceutically acceptable salt thereof, and a sufficient amount of a suitably compatible binder to produce an aminoguanidine solution;

spray-drying the aminoguanidine solution into a drying chamber under conditions sufficient to obtain a spray-dried powder suitable for direct compression into tablets; and sufficiently compressing the spray-dried powder into a compressed tablet for administration to a patient.

BRIEF DESCRIPTION OF THE DRAWINGS

FIG. 1 shows a plot of tablet hardness versus compression force for various formulations made from aminoguanidine (AMG) and Avicel® (AV) (Microcrystalline Cellulose) and 0.25% Magnesium Stearate: the circle indicates 80% AMG/20% AV tablet with a total tablet weight of 750 mg; the diamond indicates 70% AMG/30% AV tablet with a total tablet weight of 857 mg; the square indicates 60% AMG/40% AV tablet with a total tablet weight of 1000 mg; and the triangle indicates 50% AMG/50% AV tablet with a total tablet weight of 1200 mg. The black square shows about 96% Aminoguanidine HCl tablet prepared by spray drying techniques in accordance with Example 1 of the present invention.

DETAILED DESCRIPTION OF THE PREFERRED EMBODIMENTS

The development of a pharmaceutical formulation is often a laborious task. However, if the active ingredient has poor compressibility, compactibility and flow properties, the search for a large scale, economically efficient manufacturing process can be painstaking. Additionally, if the active ingredient is incompatible with excipients commonly used in pharmaceutical formulations, the task of developing the pharmaceutical formulation may require extensive experimentation. This task can be further complicated by size limitations of a tablet to be comfortably swallowed by the patient, dissolution rate limitations for bioavailablity considerations and durability requirements to successfully survive the coating process or other handling procedures. These problems were encountered and solved in the preparation of a pharmaceutical formulation for aminoguanidine.

Aminoguanidine is useful in the treatment of protein aging as disclosed in U.S. Pat. Nos. 4,758,583 and 4,665,192, incorporated by reference herein, as well as other known uses. Aminoguanidine is commercially available or easily prepared in a variety of pharmaceutically acceptable salt forms such as aminoguanidine hydrochloride, bicarbonate, hemisulfacte, nitrate, sulfate, hydrogen carbonate or dihydrochloride. The salt form is preferred over the free base, and the hydrochloride salt form is preferred among the various salt forms. "Aminoguanidine" as used herein means the free base or the various pharmaceutically acceptable salt forms unless otherwise designated. "Pharmaceutically acceptable salt" forms means any salt form which is non-toxic and permits the formulation to deliver the desired amount of active ingredient in accordance with acceptable pharmaceutical practices.

Aminoguanidine exhibits poor compressibility and compactibility, exists in a crystalline form which exhibits poor flow properties and is bitter to the taste. Compressibility means the ability of a powder to decrease in volume under pressure, while compactibility means the ability of a powder to be compressed into a tablet of a certain strength or hardness. The flow properties of a compound effect the suitability of the compound to be commercially produced. If the compound has poor flow properties, excipients may be added in order to enhance the ability of the compound to flow into hoppers, bins and other containers and/or conduits necessary in the production of a tablet formulation. However, the addition of added excipients is expensive, time consuming and can produce a tablet larger than desired and can effect stability.

An object of the present invention was to produce a pharmaceutical formulation comprising aminoguanidine for oral administration to a patient which required less than 50% excipients. Having 50% by weight of excipients was undesirable for a number of reasons, for example, this increased the size of the tablet such that high doses of aminoguanidine produced a tablet too large to be comfortably swallowed by the patient. The aminoguanidine formulation sought should be palatable and be capable of providing dosages of about 50 mg to about 1200 mg in one formulation. Other factors for determining the preferred formulation involved time and cost of manufacture, stability and bioavailability.

As used herein, the following words have the assigned meanings:

(a) "Excipient" as used herein means a substance used in combination with an active ingredient to produce a pharmaceutical formulation. Some examples of excipients are binders, lubricants, disintegrants, diluents, colorants, flavors, glidants, surfactants, absorbants and sweetening agents. Amounts of excipients to be used and methods of combining the excipient with the active ingredient are well known in the art. "Excipient" as used herein can mean one excipient or a mixture of excipients;

(b) "Binder" is an agent used to impart cohesive qualities to the powdered material. Typically, materials used as binders are water-soluble derivatives of cellulose, starches, gelatins, sugars, natural and synthetic gums, polyethylene glycol ethylcellulose, waxes, water and alcohol;

(c) "Lubricants" are agents which prevent adhesion of the tablet material to the surface of the dies and punches, reduce interparticle friction, facilitate the ejection of the tablets from the die cavity and may improve the flow rate of the tablet granulation. Commonly used lubricants include talc, magnesium stearate, calcium stearate, stearic acid, waxes, hydrogenated vegetable oils and polyethylene glycol, and most are used in concentrations of less than 1%;

(d) "Glidants" improve the flow characteristics of a powder mixture and are added in the dry state prior to compression. Commonly used glidants are colloidal silicon dioxide (Cab-o-sil from Cabot), Quso (Phia Quartz), corn starch and talc (asbestos-free);

(e) "Disintegrants" are added to a tablet to aid in the disintegration after administration. Commonly used disintegrants include starches, clays, celluloses, algins, gums and crosslinked polymers;

(f) A "suitably compatible excipient" means an excipient which is inert with aminoguanidine such that aminoguanidine remains active in order to produce the desired therapeutic effect. The examples described herein illustrate some of the suitably compatible binders, lubricants, etc., useful in accordance with the present invention. Preferably, the suitably compatible excipients are selected from the group consisting of microcrystalline cellulose, calcium stearate, hydroxypropyl cellulose, colloidal silicon dioxide, stearic acid and any other excipients compatible with aminoguanidine;

(g) "Suitable for commercial pharmaceutical use" means that large scale commercial processes can be used to produce a product which is durable enough to withstand handling procedures after the final production step or at intermediate steps in the manufacturing process such as prior to coating. If an agent is suitable for commercial pharmaceutical use it means there is negligible chipping and breaking of the product which can be measured by standard friability tests wherein the friability value is less than 1%, and a substantial amount of the product can dissolve within a specified period of time such as 70–90% of the product dissolving within 30 minutes using standard dissolution tests; and (h) "Tablet weight" as used herein means the core tablet weight, i.e., uncoated tablet weight, unless otherwise designated.

The poor compactibility and compressibility properties of aminoguanidine are illustrated in FIG. 1 which is a plot of tablet hardness versus compressive force for various aminoguanidine direct compression formulations. Using direct compression tableting methods, all of these formulations were compressed on a single station instrumented Korsch™ Model EK-0 tablet press and contain about 0.25% (wt/wt) lubricant (Magnesium Stearate NF) and 600 mg. of active ingredient aminoguanidine. In these experiments, Microcrystalline Cellulose NF (Avicel® PH-102, made by FMC Corporation of Philadelphia, Pa.) was added as a compression aid (binder). Results are shown for aminoguanidine/Avicel® mixtures respectively of 80%/20%, 70%/30%, 60%/40% and 50%/50% which result in total tablet weights respectively of 0.75 g, 0.85 g, 1.00 g and 1.20 g. Additionally, one spray-dry formulation comprising about 96% aminoguanidine made in accordance with Example 1 is shown.

These data indicate that a large amount of excipient (about 50% Avicel®) was required in order to produce a directly compressed tablet having a compression profile similar to a spray dried tablet of the present invention having about 4% excipients. (It should be noted that Avicel® also has poor flow properties which is not conducive to a commercial scale up.) At 50% aminoguanidine/50% Avicel®, the 1.2 g tablets, which contain 600 mg of the active ingredient, were considered undesirably large for human consumption.

An additional problem encountered with the addition of large amounts and/or numbers of excipients to aminoguanidine in order to overcome its inherently adverse properties to manufacturing was that a number of excipients were not compatible with this formulation. Using methods such as Differential Scanning Calorimetry, High Performance Liquid Chromatography and analysis for degradation products such as hydrazine, one may determine suitably compatible excipients.

In accordance with the present invention, spray drying techniques are used to change the characteristics of aminoguanidine sufficiently to enhance the ease of manufacturing thereof and reduce the quanitity of excipients required. It was not expected that spray drying would produce such a dramatic reduction in the amount of excipient required. A product for commercial production would contain 50%–99% aminoguanidine. Preferably, the formulation contains 80%–99%, and more preferably 95–97% aminoguanidine.

Spray drying as described herein means any method which substantially dissolves aminoguanidine in any form with a solvent which can be subsequently removed by spray drying. The solvent is preferably an aqueous solution, and, more preferably, purified water. The aminoguanidine solution may contain excipients necessary to produce a product capable of being compressed into a suitable direct compression tablet suitable for oral administration to a patient. "Patient" as used herein means any mammal such as a human being.

Spray drying may employ any spray drying equipment such as a Nifo HT, Nifo Utility (UT) Model I or Model II spray Drier, and the Nifo P6.3 Production Spray Drier manufactured by Nifo Atomizer, Inc. of Columbia, Md. Typically, spray drying techniques utilize an inlet feed tank which feeds an aqueous solution containing the active ingredient via a pump to a rotary (wheel) or nozzle atomizer or other device which produces droplets of the aqueous solution. The droplets are sprayed into a heated drying chamber wherein the water from the droplets is evaporated without injury to the active ingredient and the resulting powder collected in a collection system. Evaporation of moisture from the droplets and formation of dry particles proceed under controlled temperature and airflow conditions. This process can be optimized and controlled using data collected from experiments. With aminoguanidine, there is a physical change in the spray dried powder into spheres which can be shown by scanning electron micrographs, thus improving flow properties thereof.

As used herein, when the aminoguanidine solution is "sprayed" into a drying chamber, the aminoguanidine is delivered in any manner which can produce the powder suitable for direct compression techniques. The "drying chamber" can be any space sufficient to evaporate the solvent to produce the desired powder.

In accordance with the present invention, the aminoguanidine solution comprises aminoguanidine, preferably aminoguanidine in a salt form, and more preferably the hydrochloride salt form, from about 10% to about 75% weight/weight of the solution, and a suitably compatible excipient, preferably a binder from about 0.1% to about 20% weight/weight of the solution, and a sufficient amount of an aqueous solution to substantially dissolve the aminoguanidine. Typically, the aqueous solution is purified water and is from about 25% to about 90% weight/weight of the aminoguanidine solution.

Preferably, the aminoguanidine is from about 30% to about 50% weight/weight of the aminoguanidine solution, and, more preferably from about 38 to about 42% weight/weight of the aminoguanidine solution.

Preferably, the suitably compatible binder is from about 0.2% to about 3.0% weight/weight of the aminoguanidine solution, and, more preferably from about 1.0% to about 2.0% weight/weight of the aminoguanidine solution.

Preferably, the aqueous solution is from about 45% to about 70% weight/weight of the aminoguanidine solution, and, more preferably from about 55% to about 60% weight/weight of the aminoguanidine solution.

The aminoguanidine solution may be prepared by any method which permits substantial dissolution of aminoguanidine and preferably also the binder such as keeping the ingredients admixed overnight or heating the solution to about 30° C. for about 30 minutes. The order of mixing ingredients is preferably water, aminoguanidine and excipients. "Substantial dissolution" means that the aminoguanidine has dissolved sufficiently in the solution such that formulations may be prepared therefrom which will contain a uniform amount of aminoguanidine in each formulation and have the desired bioavailability in accordance with guidelines acceptable to the pharmaceutical industry.

After the aminoguanidine solution has been fed into the spray drying apparatus at a controlled temperature and airflow, the resulting powder is then subjected to direct compression tableting methods. Preferably, other excipients such as glidants and lubricants are blended into the powder by known methods to enhance the ease of the direct compression tabletting procedure. For example, Colloidal Silicon Dioxide NF and/or Calcium Stearate can be added, each in amounts between about 0.1% to about 1.5% weight/weight.

The resulting powder will contain over 50% aminoguanidine weight/weight. Typically, the resulting powder collected after spray drying comprises from about 80% to about 99.8% weight/weight, and preferably from about 90% to about 99% weight/weight, and, more preferably, from about 95% to about 97% weight/weight of aminoguanidine, preferably an aminoguandine salt such as hydrochloride salt; and from about 0.2% to about 20% weight/weight, and preferably from about 1.0% to about 10% weight/weight, and, more preferably, from about 2% to about 4.75% weight/weight of a suitably compatible excipient such as a binder. The resulting compressed tablet may also have the same or substantially the same percentage weights as the powder depending upon whether other excipients are added.

Direct compression tablet methods for formulating dosage forms produces a highly cost effective product. Typically, this method involves compressing the active ingredient, usually in the presence of excipients into a tablet of sufficient hardness capable of withstanding chipping and breaking and/or subsequent processes such as coating processes. The compression is accomplished by equipment well known in the art and the hardness of tablets is tested by known methods as described, for example, in Remington's Pharmaceutical Sciences, 18th ed., Mack Publishing Company 1990, incorporated herein by reference.

Since aminoguanidine is bitter to the taste, it is desirable to coat the tablet containing aminoguanidine to cover the taste thereof. Examples of acceptable commercial coating processes are described in "The Theory and Practice of Industrial Pharmacy, 3rd, ed", Lachman Lieberman, Kanig, pp. 359–373, incorporated herein by reference.

The tablet must be of sufficient hardness to withstand the coating process without chipping or breaking. The hardness of the tablets prepared in accordance with the present invention can be measured by any standard method such as the Schleuniger tablet hardness tester, described in Theory and Practice of Industrial Pharmacy, 3rd ed., pp. 297–298, incorporated herein by reference. Another measure of durability of the tablet is the test for friability. See Lachman, Lieberman and Kanig's *Theory and Practice of Industrial Pharmacy*. The resistance to surface abrasions is exemplified by tests which measure weight loss of the tablet on subjecting the tablets to standized agitation procedures such as provided by the Roche Friabilator where the initial weight ($W_o$) of tablets subjected to 100 free falls of 6 inches in a rotating drum are then weighed (W). The friability, f, is given by:

$$f = 100 \times (1 - W/W_o)$$

Values of from 0.8 to 1.0% are regarded as the upper limit of acceptability. Typically, a value of less than 0.5% is preferred.

With or without the coating, the tablet made as described herein should be an immediate release formulation. Immediate release formulation means that a substantial portion of the tablet, e.g., 70–90%, will dissolve within 30 minutes using standard dissolution tests such as the USP Dissolution Test.

The following experiments are intended to provide those skilled in the art with descriptions of the present invention without intending to limit what the inventors regard as their invention. Unless otherwise stated, all measurements are percentage weight/weight, all temperatures in degrees C, and pressure is at or near atomospheric pressure.

EXAMPLE 1

| | |
|---|---|
| Aminoguanidine HCl Dow Chemical Co. | 62.2 kg |
| HPC (Hyroxypropyl cellulose, LF) Aqualon | 1.9 kg |
| Deionized water | 91.3 kg |

Equipment: Niro™ Utility spray dryer with a chamber 4.0 feet in diameter and 2.5 feet cylindrical height and a 120 mm low vaned wheel. Ambient air is used as drying gas which is electrically heated. The drying gas enters the chamber through a roof air disperser. Gases and entrained powder leave the chamber and pass through a cyclone separator. Product is collected at the cyclone. The feed tank is provided with an agitator and heating jacket. A Moyno™ pump delivers the feed to the rotary atomizer in the top of the chamber, spraying downward. Air temperatures are measured by capillary bulb thermocouples. Ports on the conical sides allowed manual rapping to remove loose deposits.

The aminoguanidine HCl was dissolved in the water and then the HPC was added. The batch was allowed to agitate overnight producing the aminoguanidine solution. An inspection of the batch prior to spray drying showed that some undissolved crystals had settled on the bottom of the tank. The aminoguanidine solution had about 36% to 38% solids.

For each of the following runs, there was an atomizer velocity of 24,000 rpm and a drying air rate of 365 kg/hr:

1.A The aminoguanidine solution was spray dried at a feed rate of 39.6 kg/hr, at an inlet temperature of 300 degrees, and an outlet temperature of 90 degrees producing a product wherein 90% is less than 174 microns, 50% is less than 85 microns and 10% is less than 33 microns.

1.B The aminoguanidine solution was spray dried at a feed rate of 24.2 kg/hr, at an inlet temperature of 200 degrees, and an outlet temperature of 80 degrees producing a product wherein 90% is less than 137 microns, 50% is less than 59 microns and 10% is less than 23 microns.

1.C The aminoguanidine solution was spray dried at a feed rate of 27.6 kg/hr, at an inlet temperature of 200 degrees, and an outlet temperature of 70 degrees producing a product wherein 90% is less than 141 microns, 50% is less than 62 microns and 10% is less than 22 microns.

The end product spray dried powder had a moisture content of less than 0.1%, a loose density of about 0.36 g/cc and an average size ranging from 59 to 85 microns. It was easily compressible producing a compressed tablet with good friability and a disintegration time of about 5 minutes.

The spray dried powder from preparation 1.A was compressed into tablets weighing 623.44 mg and containing Aminoguanidine HCl 600 mg and Hydroxypropyl Cellulose LF, NF 18.76 mg, Cab-O-Sil™ 3.12 mg, and Calcium Stearate 1.56 mg.

EXAMPLE 2

| | |
|---|---|
| Aminoguanidine HCl | 40% |
| HPC | 1.25% |
| Deionized water | 58.75 |

Using methods analogous to example 1, the foregoing ingredients were mixed to make an aminoguanidine solution which was fed into a Niro™ model HT spray drier at an inlet temperature of 230 degrees, atomizer pressure of 5 Bar psi, feed flow rate of 70–77 gm/min. Three batches were prepared.

The product yields on all batches were around 95% with about 90% of the yield collected in the chamber and 10% of the yield collected in the cyclone. The product was analyzed using scanning electron microscopy. A comparison of the untreated aminoguanidine HCl (in crystalline form) with the spray dried product showed the latter to be hollow spheres which decreased the density of the powder and enhanced the flow properties thereof.

EXAMPLE 3

Using methods analogous to Example 1, the following aminoguanidine solution was prepared and spray dried to prepare a powder to which was added the calcium stearate and colloidal silicon dioxide. Tablets were compressed using standard tablet compression techniques.

These tablets were then coated with 20% solution of OPADRY II™ from Colorcon, Inc. of Westport, Pa. in deionized water to a 3% theoretical weight gain.

| INGREDIENT | AM. SOLN. W/W % | TABLET % W/W | TABLET mg |
|---|---|---|---|
| Aminoguanidine HCl | 40.0 | 96.24 | 300 |
| Hydroxypropyl Cellulose, LF, NF | 1.25 | 3.01 | 9.38 |
| Deionized water | 58.75 | — | — |
| Colloidal Silicon Dioxide, NF (Cab-O-Sil ™) | — | 0.50 | 1.56 |
| Calcium Stearate, NF | — | 0.25 | 0.78 |
| TOTAL | 100 | 100 | 311.72 |

EXAMPLE 4

In order to determine suitably compatible excipients to be admixed with aminoguanidine, aminoguanidine can be studied with a variety of excipients in standard tests such as the following:

Differential Scanning Calorimetry (DSC)

This is a method of thermal analysis and is useful in the investigation of solid-state interactions. Initial investigation includes determining endo or exotherms displayed by the individual components followed by generating scans of a mixture of the active and excipient. Possible interations are indicated by the addition or disappearance of one or more new peaks (endo or exotherms). In the absence of interaction, the endo or exotherms exhibited by the pure materials (excipient and active) is evident in scans of the mixture (although small shifts in termperature are common and are often related to the ratio of active to excipient). Interpretation of such thermal data is preferably supported by additional assay data such as HPLC. Scans can be recorded from 30° to 200° C. at a rate of 10° C. per minute.

High Performance Liquid Chromatography (HPLC)

HPLC can be performed on the mixture of excipient and active at each time point in an effort to quantirate loss of active (% recovery). At each time point, samples can be removed from stressed conditions and diluted to volume with deionized, distilled water (except the more highly hydrophobic samples which had a fixed volume added). These samples can be diluted further to an appropriate concentration for HPLC analysis.

Analysis for Hydrazine

The possible degradation of aminoguanidine to hydrazine can be monitored via HPLC with pulsed electrochemical detection.

Observations

In addition to the more quantitative assays, observations such as color and physical state (deliquescence) can be noted.

EXAMPLE 5

Equipment: Niro™ custom built spray dryer which had a ten foot diameter and a ten foot high straight section that sat on top of a 60 degree right cylindrical cone. It was equipped with a 24 Hi vane Niro™ atomizer that is 120 mm in diameter.

The inlet temperature was 230° C., outlet temperature was 90° C., solution feed rate was 185 kg/hr, air flow rate was 2300 kg of bone dry air per hour. (The preceeding parameters may vary somewhat.) The atomizer was revolving at 20,000 rpm and the spray dryer was equipped with a pneumatic collection system. Using methods analogous to Example 1, aminoguanidine HCl and hydroxypropyl cellulose were substantially dissolved in purified water and spray dried to produce a powder from which compressed tablets, as defined herein, containing 200 mg and 400 mg of aminoguanidine were prepared.

| INGREDIENT PER TABLET | | |
|---|---|---|
| Aminoguanidine HCl | 200 mg | 400 mg |
| Hydroxypropyl Cellulose, LF, NF | 6.25 mg | 12.51 mg |
| Collidal Silicon Dioxide NF (Cab-O-Sil ™) | 1.04 mg | 2.08 mg |
| Calcium Stearate, NF | 0.52 mg | 1.04 mg |
| TOTAL TABLET WEIGHT | 207.81 mg | 415.63 mg |

What is claimed is:

1. A method of making a direct compression tablet suitable for commercial pharmaceutical use comprising between about 50% to about 99% aminoguanidine or pharmaceutically acceptable salt thereof by weight of the tablet comprising:

combining a sufficient amount of aminoguanidine or a pharmaceutically acceptable salt thereof, a sufficient amount of a solvent capable of substantially dissolving the aminoguanidine or pharmaceutically acceptable salt thereof, and a sufficient amount of a suitably compatible binder to produce an aminoguanidine solution;

spray-drying the aminoguanidine solution into a drying chamber under conditions sufficient to obtain a spray-dried powder suitable for direct compression into tablets; and sufficiently compressing the spray-dried powder into a compressed tablet for administration to a patient.

2. The method of claim 1 wherein the aminoguanidine salt is aminoguanidine hydrochloride.

3. The method of claim 1 wherein the amount of aminoguanidine is from about 80% to about 99% weight by weight of the tablet.

4. The method of claim 1 wherein the amount of aminoguanidine is from about 95% to about 97% weight by weight of the tablet.

5. The method of claim 1 further comprising adding an effective amount of a suitably compatible excipient to the spray-dried powder.

6. The method of claim 5 wherein the excipients are selected from the group consisting of micro-crystalline cellulose, calcium stearate, hydroxypropyl cellulose, colloidal silicon dioxide and stearic acid.

7. The method of claim 5 wherein the aminoguanidine is aminoguanidine hydrochloride present in an amount of from about 95 to about 77%, the binder is hydroxypropyl cellulose, and the excipients are colloidal silicon dioxide and calcium stearate.

8. The method of claim 1 wherein the binder is a water soluble cellulose.

9. The method of claim 7 wherein the binder is hydroxypropyl cellulose.

10. A direct-compression tablet comprising from about 50% to about 99% aminoguanidine or pharmaceutically acceptable salt thereof for administration to a patient prepared by a process comprising the steps of:

combining a sufficient amount of aminoguanidine or a pharmaceutically acceptable salt thereof, a sufficient amount of a solvent capable of substantially dissolving the aminoguanidine or pharmaceutically accetpable salt thereof, and a sufficient amount of a suitably compatible binder to produce an aminoguanidine solution;

spray-drying the aminoguanidine solution into a drying chamber under conditions sufficient to obtain a spray-dried powder suitable for direct compression into tablets; and sufficiently compressing the spray-dried powder into a compressed tablet for administration to a patient wherein the direct-compression tablet comprises from about 50% to about 99% aminoguanidine or a pharmaceutically acceptable salt thereof.

11. The direct-compression tablet of claim 10 wherein the salt form is aminoguanidine hydrochloride.

12. The direct-compression tablet of claim 10 wherein the amount of aminoguanidine is from about 80% to about 99%.

13. The direct-compression tablet of claim 10 wherein the amount of aminoguanidine is from about 95% to about 97%.

14. The direct-compression tablet of claim 10 further comprising adding a sufficient amount of a suitably compatible excipient to the spray-dried powder.

15. The direct-compression tablet of claim 14 wherein the excipients are selected from the group consisting of micro-crystalline cellulose, calcium stearate and colloidal silicon dioxide, and stearic acid.

16. The direct-compression tablet of claim 14 wherein the aminoguanidine is aminoguanidine hydrochloride present in an amount of from about 95 to about 97%, the binder is hydroxypropyl cellulose, and the excipients are colloidal silicon dioxide and calcium stearate.

17. The direct-compression tablet of claim 10 wherein the tablet has a friability value less than 1%.

18. The direct-compression tablet of claim 10 wherein the binder is a water soluble cellulose.

19. The direct-compression tablet of claim 10 wherein the binder is hydroxypropyl cellulose.

20. The method of claim 1 wherein the solvent is an aqueous solution.

21. The tablet of claim 10 wherein the solvent is an aqueous solution.

* * * * *

UNITED STATES PATENT AND TRADEMARK OFFICE
CERTIFICATE OF CORRECTION

PATENT NO.   :   5,534,551

DATED        :   July 9, 1996

INVENTOR(s)  :   Phillip E. Page, et al.

It is certified that error appears in the above-identified patent and that said Letters Patent is hereby corrected as shown below:

```
column 5, line 12, "Nifo HT Utility" should read -- Niro HT, Niro Utility--.
column 5, line 13, "Nifo P6.3" should read -- Niro P6.3--
Column 5, line 14, "Nifo Atomizer" should read -- Niro Atomizer --
```
column 6, line 55, the patent reads "standized" and should read --standardized--.
column 8, line 67, the patent reads "termperature" and should read --temperature--.
column 9, line 9, the patent reads "quantirate" and should read --quantitate-- .
column 10, line 23, (claim 7, line 3) the patent reads "95 to about 77%" and should read --95 to about 97%--.

Signed and Sealed this

Sixteenth Day of September, 1997

*Attest:*

BRUCE LEHMAN

*Attesting Officer*   *Commissioner of Patents and Trademarks*